United States Patent [19]

Gradeff et al.

[11] Patent Number: 4,703,109
[45] Date of Patent: * Oct. 27, 1987

[54] TRICYCLOPENTADIENYL CERIUM AND PROCESS FOR PREPARING THE SAME

[75] Inventors: Peter S. Gradeff, Pottersville; Fred G. Schreiber, Highland Park, both of N.J.

[73] Assignee: Rhone-Poulenc, Inc., New Brunswick, N.J.

[*] Notice: The portion of the term of this patent subsequent to Jan. 8, 2002 has been disclaimed.

[21] Appl. No.: 674,639

[22] Filed: Nov. 26, 1984

Related U.S. Application Data

[63] Continuation-in-part of Ser. No. 604,756, Apr. 27, 1984, Pat. No. 4,492,655.

[51] Int. Cl.$^4$ .............................................. C07F 17/00
[52] U.S. Cl. ..................................................... 534/15
[58] Field of Search ........................... 534/15; 556/143

[56] References Cited

U.S. PATENT DOCUMENTS

| | | | |
|---|---|---|---|
| 2,818,416 | 12/1957 | Brown et al. | 534/15 |
| 4,492,655 | 1/1985 | Gradeff et al. | 534/15 |
| 4,511,515 | 4/1985 | Thompson | 534/15 |

OTHER PUBLICATIONS

H. Gysling, "Organolanthanides and Organoactinides", Advances in Organometallic Chem., vol. 9, Stone et al., [Ed.], Academic Press, N.Y., 1970, pp. 365–376.
G. B. Deacon et al., "Refutation of the Synthesis of Tetrakis(cyclopentadienyl) Cerium (IV); *Polyhedron*, vol. 2(9), 1983, p. 969.
Kalsotra et al., J. Organometal. Chem., 1971, 28(1), p. 87.
Wilkinson et al., J. Am. Chem. Soc., 76 (1954), 6210.

*Primary Examiner*—John F. Terapane
*Assistant Examiner*—Virginia B. Caress

[57] ABSTRACT

A process is provided for preparing tricyclopentadienyl cerium as well as the mono and dicyclopentadienyl cerium intermediates which comprises reacting an alkali metal cyclopentadienide with ceric ammonium nitrate, in solution in an inert organic solvent in a manner to obtain either tricyclopentadienyl cerium or to form in sequence, and stepwise, monocyclopentadienyl cerium dinitrate, dicyclopentadienyl cerium mononitrate, and tricyclopentadienyl cerium, depending upon the order of addition of the reactants.

10 Claims, No Drawings

TRICYCLOPENTADIENYL CERIUM AND PROCESS FOR PREPARING THE SAME

This application is a continuation-in-part of Ser. No. 604,756, filed Apr. 27, 1984, and now U.S. Pat. No. 4,492,655.

Wilkinson and Birmingham *Journal of the American Chemical Society* 76 6210 (1954) have pointed out that cyclopentadiene forms organometallic compounds with a number of metals, to which the cyclopentadiene ring may be attached in three ways:

(a) by the two electron covalent bond, which may be referred to as the "sandwich bond", to many transitional metals.

(b) by a covalent bond between the metal and a single carbon atom of the ring. The silicon cyclopentadienyl compounds may be of this type.

(c) by ionic bonds.

By stirring the anhydrous chloride of the metal with cyclopentadienyl sodium in tetrahydrofuran solution, removing the solvent, and then heating the residue at 200° to 250° C. in vacuum, tricyclopentadienyl metal compounds of the formula $(C_5H_5)_3M$ will form, in which M includes cerium (III). Tricyclopentadienyl cerium (III) is a crystalline solid, thermally stable to at least 435° C., at which it melts, decomposing with water to give cyclopentadiene and cerous hydroxide, and soluble in tetrahydrofuran and glycol dimethyl ether. Tricyclopentadienyl cerium reacts rapidly with air, blackening instantaneously even with only traces of oxygen. Further details on this work appear in the article by Birmingham and Wilkinson *Journal of the American Chemical Society,* 78 42 (1956).

Kalsotra, Anand, Multani, and Jain *Journal of Organometallic Chemistry* 28 87–89 (1971) reported the preparation of tetracyclopentadienyl cerium by reaction of cyclopentadienyl sodium in tetrahydrofuran with dipyridinium cerium hexachloride. The reaction was carried out under anhydrous conditions. The sodium cyclopentadienide was added to a solution of the dipyridinium cerium hexachloride in tetrahydrofuran, and the mixture kept at reflux at 100° to 110° C. with vigorous stirring for ten to twelve hours, until a reddish brown product formed. The cooled mixture was filtered through a sintered glass disc, and the residue washed with tetrahydrofuran. Evaporation of the solvent yielded a thick brown paste, which was crystallized from light petroleum ether, yielding a red-orange crystalline compound, strikingly similar in color to the tricyclopentadienyl cerium reported by Birmingham and Wilkinson in 1956. Further information on the preparation is given in *Israel Journal of Chemistry,* 9,569–572 (1971).

In a further series of papers, Kalsotra and coworkers reported on thio derivatives of tricyclopentadienyl cerium (IV) (*Journal of Inorganic Nuclear Chemistry,* 35,3966–3968 (1973)); pseudohalide complexes of tricyclopentadienyl cerium (IV) (*Journal of Inorganic Nuclear Chemistry,* 34,2265–2269 (1972)); alkoxy derivatives of cerium (IV) (*Journal of Organometallic Chemistry,* 63,301–303 (1973)); phenolic derivatives of tricyclopentadienyl cerium (IV) (*Journal of the Chinese Chemical Society,* 19,197–202 (1972)); carboxylato complexes of tricyclopentadienyl cerium (IV) chloride (*Journal of the Chinese Chemical Society,* 18,189–197 (1971)); and alkoxy derivatives of tricyclopentadienyl cerium IV (*Journal of the Chinese Chemical Society,* 20,171–173 (1973)).

However, Deacon, Tuong and Vince *Polyhedron,* 2,969–970 (1983) refuted the synthesis of tetrakis(cyclopentadienyl)cerium (IV) by these workers, showing that the reaction of sodium cyclopentadienide with dipyridinium hexachlorocerate (IV) in tetrahydrofuran yields tris(cyclopentadienyl)cerium (III), and not tetrakis(cyclopentadienyl)cerium (IV). Deacon et al showed that the properties of a derivative, tricyclopentadienyl cerium propoxy, from this source differs in color, volatility and IR absorption from the same compound prepared by alcoholysis of tetracyclopentadienyl cerium or tricyclopentadienyl cerium chloride, and further noted that it is not easy to reconcile cleavage of tetracyclopentadienyl cerium by isopropanol with stability to water and dilute acids.

Deacon et al repeated the Kalsotra et al synthesis, and found the reaction product to be tricyclopentadienyl cerium, not tetracyclopentadienyl cerium.

The method provided by Bradley et al, *J. Chem. Soc.* 1956, 2260 was used by Kalsotra et al and also by Deacon et al to prepare dipyridinium hexachlorocerate (IV). The method is tedious, but according to the authors the only way to get a product of satisfactory quality. Cerium dioxide is first converted to ceric ammonium sulphate. Pure ceric hydroxide is precipitated from an aqueous solution of ceric ammonium sulphate and washed thoroughly. The freshly-prepared hydroxide, suspended in absolute alcohol, is treated with anhydrous hydrogen chloride and then pyridine added, which forms the insoluble dipyridinium cerium hexachloride complex $(PyH)_2CeCl_6$. The complex is filtered and dried. This complex was used for preparing the alkoxides by Bradley et al, and the cerium cyclopentadienyl derivatives by Kalsotra et al and Deacon et al.

In accordance with the present invention ceric ammonium nitrate, a commercially available material that is relatively inexpensive, is used instead of dipyridinium hexachlorocerate for preparing cerium III cyclopentadienyls in good yield. In the course of the process, cerium IV is reduced to cerium III.

The process of the invention for preparing tricyclopentadienyl cerium as well as the mono and dicyclopentadienyl cerium intermediates comprises reacting an alkali metal cyclopentadienide with ceric ammonium nitrate in solution in an inert organic solvent in a manner to obtain either tricyclopentadienyl cerium or to form in sequence, and stepwise, monocyclopentadienyl cerium dinitrate, dicyclopentadienyl cerium mononitrate, and tricyclopentadienyl cerium, depending upon the order of addition of the reactants.

When alkali metal cyclopentadienide is added into a solution of ceric ammonium nitrate, there is formed, in sequence, and stepwise, monocyclopentadienyl cerium dinitrate, $CeCp(NO_3)_2$, dicyclopentadienyl cerium mononitrate, $CeCp_2NO_3$, and tricyclopentadienyl cerium, $CeCp_3$.

When alkali metal cyclopentadienide such as sodium cyclopentadienide, NaCp, is added to a solution of ceric ammonium nitrate, several reactions can take place more or less concurrently:

(a)
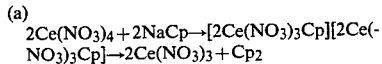

(b) $NH_4NO_3 + NaCp \rightarrow NaNO_3 + NH_3 + CpH$ (c)
$$2Ce(NO_3)_4 + 2CpH + 2NH_3 \rightarrow 2Ce(NO_3)_3 + Cp_2 + CP_2 + 2NH_4NH_4NO_3$$

(d) $Ce(NO_3)_3 + NaCp \rightarrow Ce(NO_3)_2Cp + NaNO_3$ (e) $Ce(NO_3)_2Cp + NaCp \rightarrow Ce(NO_3)Cp_2 + NaNO_3$ (f) $Ce(NO_3)Cp_2 + NaCp \rightarrow Ce(Cp)_3 + NaNO_3$ The overall reaction equation is thus:

$$2[Ce(NO_3)_4 \cdot 2NH_4NO_3] + 12NaCp \rightarrow 2Ce(Cp)_3 + 4CpH + (Cp)_2 + 12NaNO_3 + 4NH_3$$

These reactions give a tentative idea of the possible mechanism, which may or may not follow this pattern.

For instance, reaction (b) does not seem to be very fast; the evolution of ammonia can be seen along after all other reactions are completed. Reaction (a) appears to be the fastest one. In fact, there is evidence that this reaction has to go to completion before any of the other reactions can take place.

When the order of additiona is reversed, and a solution of ceric ammonium nitrate in an inert organic solvent is added to a slurry of alkali metal cyclopentadienide in an inert organic solvent, although the reactions are complex, the end product is Ce(Cp)$_3$ directly, without observation of the intermediate stages.

The process is preferably carried out by adding a solution of ceric ammonium nitrate in an inert organic solvent to a slurry of an alkali metal cyclopentadienide in the same solvent.

Any alkali metal cyclopentadienide can be used, such as sodium cyclopentadienide, potassium cyclopentadienide, caesium cyclopentadienide and lithium cyclopentadienide. Sodium cyclopentadienide is preferred. An excess of NaCp above theoretical results in formation of dark purple soluble complexes, which are not of interest. One can recover the desired Ce(Cp)$_3$ by adding the necessary amount of ceric ammonium nitrate to the complex.

When Ce(Cp)$_3$ is the desired end product, it would be easier to add the solution of ceric ammonium nitrate into the slurry of NaCp than the reverse. Obviously, then, the purple complex will be in evidence through most of the reaction time, so long as the NaCp is in excess.

The reaction can be carried out in any suitable inert organic solvent for the ceric ammonium nitrate. The alkali metal cyclopentadienide can be in solution or slurried in the same solvent. Tetrahydrofuran and dimethoxyethane are readily available, and are preferred. Other solvents which can be used include benzene, hexane, acetonitrile, and other glycol ethers.

The reaction will proceed at room temperature. Lower temperatures, ranging from about −10° to about 25° C., can be used, but then the reaction will usually be slow. The reaction proceeds also at elevated temperatures up to about 250° C., most conveniently at the reflux temperature of the solvent. The reaction proceeds quickly and is usually complete within one hour, up to about ten hours.

The reaction mixture contains the corresponding nitrate of the alkali metal, such as sodium nitrate. This salt is insoluble in the reaction medium, and will precipitate. The nitrate salt can be separated by filtration and the filtrate recovered, the solvent evaporated, and the solid residue washed and dried, to recover mono, di or tricyclopentadienyl cerium, according to the stage to which the reaction was carried.

For some applications, the mono, di or tricyclopentadienyl cerium can be used in the form in which it exists in the reaction mixture at the end of the reaction, without actually isolating it from the reaction mixture, or separating it from the by-products, which saves processing and handling costs.

The following Examples in the opinion of the inventors represent preferred embodiments of the invention:

EXAMPLE 1

Sodium cyclopentadienide was prepared by adding in 5 ml portions a solution of cyclopentadiene (12.56 g, about 95%, 0.1805 mole) in dimethoxyethane (27.1 g) at −78° C. to a slurry of sodium hydride (7.45 g, 0.1820 mole, 58.62% oil dispersion) in dimethoxyethane (98.2 g) under argon at −2° C. The temperature of the reaction mixture was kept between −10° and −20° C. by a cooling bath. Hydrogen evolution was very vigorous. After addition was complete, the gray-pink slurry of sodium cyclopentadienide was allowed to warm up to room temperature.

To a solution of ceric ammonium nitrate (0.0301 mole, 16.70 g) in 136.9 g dimethoxyethane under argon was added slowly a slurry of sodium cyclopentadienide (0.18 mole) in 125 g of dimethoxy ethane. The reaction was carried out at room temperature. A mildly exothermic reaction occurred, but cooling was unnecessary. The final reaction mixture was a dark gold-brown slurry. The mixture was stirred overnight.

The following day, the precipitate was filtered off, washed with dimethoxyethane until no more color was removed, and then dried under vacuum to give 16.0 g light tan solid almost totally soluble in water showing trace of cerium and pH about 6.5, indicating that this was the expected sodium nitrate (theoretical 15.3 g), all cerium being in the organic layer.

The filtrate was a gold brown solution in dimethoxy ethane of tricyclopentadienyl cerium. The tricyclopentadienyl cerium was recovered after evaporating the solvent.

EXAMPLE 2

0.061 mole of Na cyclopentadienide was suspended in 150 ml dimethoxy ethane. This was added over 15 minutes into a solution of 0.03 mole of cerium ammonium nitrate in 150 ml dimethoxy ethane at room temperature. Reaction was rapid, and the solid NaNO$_3$ that separated was filtered off after 15 minutes.

The filtrate contained Ce(NO$_3$)$_2$Cp. The dimethoxy ethane was evaporated from one portion of the solution and the solid recovered.

To the remaining portion of the solution was added 2 mole equivalents of NaAc per mole equivalent of Ce(NO$_3$)$_2$Cp. Reaction was rapid, producing 2 moles NaNO$_3$ and 1 mole Ce(Ac)$_2$Cp. This was filtered off as a solid mixture. The Ce(Ac)$_2$Cp was separated from the NaNO$_3$ by methanol trituration.

EXAMPLE 3

0.061 mole Na cyclopentadienide was suspended in 150 ml dimethoxy ethane. This was added over 15 minutes into a solution of 0.03 mole of cerium ammonium nitrate in 150 ml dimethoxy ethane at room temperature. Reaction was rapid, and the solid NaNO$_3$ that separated was filtered off after 15 minutes.

The filtrate contained Ce(NO₃)₂Cp. The dimethoxy ethane was evaporated from one portion of the solution and the solid recovered.

To the remaining portion of the solution was added 2 mole equivalents of Na octoate per mole equivalent of Ce(NO₃)₂Cp. Reaction was rapid, producing 2 moles NaNO₃ and 1 mole Ce(oct)₂Cp. The NaNO₃ was separated by filtration. The Ce(Oct)₂Cp was isolated by evaporation of the solvent.

EXAMPLE 4

0.091 mole Na cyclopentadienide was suspended in 150 ml dimethoxy ethane. This was added over 15 minutes into a solution of 0.03 mole of cerium ammonium nitrate in 150 ml dimethoxy ethane at room temperature. Reaction was rapid, and the solid NaNO₃ that separated was filtered off after 15 minutes.

The filtrate contained CeNO₃(Cp)₂. The dimethoxy ethane was evaporated from one portion of the solution and the solid recovered.

To the remaining portion of the solution was added 1 mole equivalent of NaAc per mole equivalent of CeNO₃(Cp)₂. Reaction was rapid, producing 1 mole NaNO₃ and 1 mole CeAc(Cp)₂. This was filtered off as a solid mixture. The CeAc(Cp)₂ was separated by trituration with methanol.

EXAMPLE 5

0.061 mole Na cyclopentadienide was suspended in 150 ml dimethoxy ethane. This was added over 15 minutes into a solution of 0.03 mole of cerium ammonium nitrate in 150 ml dimethoxy ethane at room temperature. Reaction was rapid, and the solid NaNO₃ that separated was filtered off after 15 minutes.

The filtrate contained Ce(NO₃)₂Cp. The dimethoxy ethane was evaporated from one portion of the solution and the solid recovered.

To the remaining portion of the solution was added 2 mole equivalents of

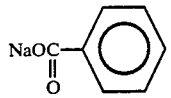

per mole equivalent of Ce(NO₃)₂Cp. Reaction was rapid, producing 2 moles NaNO₃ and 1 mole

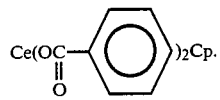

This was filtered off as a solid mixture. The

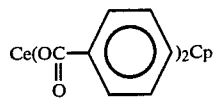

was separated by trituration with methanol.

EXAMPLE 6

To a suspension of 0.1805 mole of NaCp in tetrahydrofuran there was added slowly a solution of ceric ammonium nitrate, 0.03 mole, in 100 g dimethoxyethane. The reaction mixture showed a deep purple color, then dark-gold brown by the end of the addition of ceric ammonium nitrate. After refluxing overnight the evolution of NH₃ had subsided. The resulting NaNO₃ was filtered, and the Ce(Cp)₃ recovered from the solution.

Having regard to the foregoing disclosure, the following is claimed as the inventive and patentable embodiments thereof:

1. A process for preparing tricyclopentadienyl cerium, which comprises reacting an alkali metal cyclopentadienide with ceric ammonium nitrate in solution in an inert organic solvent until tricyclopentadienyl cerium is formed.

2. A process according to claim 1, in which a solution of ceric ammonium nitrate is added to the alkali metal cyclopentadienide.

3. A process according to claim 2 in which the alkali metal cyclopentadienide is in the form of a slurry in the same organic solvent.

4. A process according to claim 1, in which the temperature is within the range from about −10° to about 250° C.

5. A process according to claim 1, in which the alkali metal cyclopentadienide is added to the solution of ceric ammonium nitrate.

6. A process according to claim 5 in which the alkali metal cyclopentadienide is in the form of a slurry in the same organic solvent.

7. A process according to claim 5, in which the temperature is within the range from about −10° to about 250° C.

8. A process according to claim 1 in which the reaction is carried out at the reflux temperature of the inert organic solvent.

9. A process according to claim 1 in which the alkali metal cyclopentadienide is sodium cyclopentadienide.

10. A process according to claim 1 in which alkali metal nitrate formed in the reaction is separated out by filtration and cyclopentadienyl cerium recovered from the filtrate.

* * * * *